United States Patent
Arstad

(10) Patent No.: US 8,614,360 B2
(45) Date of Patent: Dec. 24, 2013

(54) METHOD FOR THE PREPARATION OF [$^{18}$F]FLUOROALKYLHALIDES

(75) Inventor: Erik Arstad, London (GB)

(73) Assignee: Hammersmith Imanet Limited, London (GB)

(*) Notice: Subject to any disclaimer, the term of this patent is extended or adjusted under 35 U.S.C. 154(b) by 1085 days.

(21) Appl. No.: 12/096,417

(22) PCT Filed: Dec. 8, 2006

(86) PCT No.: PCT/NO2006/000473
§ 371 (c)(1),
(2), (4) Date: Oct. 14, 2008

(87) PCT Pub. No.: WO2007/067074
PCT Pub. Date: Jun. 14, 2007

(65) Prior Publication Data
US 2009/0247793 A1    Oct. 1, 2009

(30) Foreign Application Priority Data
Dec. 8, 2005 (GB) .................................. 0524988.3

(51) Int. Cl.
C07C 19/08  (2006.01)
C07C 17/00  (2006.01)
C07C 21/18  (2006.01)
C07C 23/00  (2006.01)
C07C 25/13  (2006.01)

(52) U.S. Cl.
USPC .............................. 570/134; 570/123; 570/170

(58) Field of Classification Search
None
See application file for complete search history.

(56) References Cited

U.S. PATENT DOCUMENTS 5,057,470 A   10/1991   Kellner
5,300,712 A   4/1994    Baker

FOREIGN PATENT DOCUMENTS

JP   5017379       1/1993
WO   2004/029006   4/2004
WO   2004/056726   7/2004

OTHER PUBLICATIONS

Nystrom, R. Journal of the American Chemical Society, 1954, 77, 2544-2545.*
O'Conner et al. J. Org. Chem. 1992, 57, 5075-5077.*
Baird et al. Dalton Transactions, 1977, 1576-1582.*
Zhang, et.al. "Development of an automated system for synthesizing 18F-labeled compounds using [18F]fluorethyl bromide as a synthetic precursor" Applied Radiation and Isotopes, vol. 57, 2002, pp. 335-342.
Sobrio, et.al. "Radiosynthesis of [18F]Lu29-024: A potential PET ligand for brainimaging of the serotonergic 5-HT2 receptor" Bioorganic and Medicinal Chemistry, vol. 8, 2000, pp. 2511-2518.
Tsuji, et.al. "Organic synthesis by means of noble metal compounds. XXIX. Decarbonylation of acid halides and carbonylation of alkyl halides catalyzed by rhodium complex" Tetrahedron Letters, vol. 39, 1966, pp. 4713-4716.
Holub, et.al. The action of elementary fluorine upon organic comopunds. XV. Fluoride and cobaltic fluoride as fluorinating agents for ketones, 1950, pp. 4879-4884.
PCT/NO2006/000473 Int'l Search Report and Written Opinion dated May 2007.
GB0524988.3 Search Report dated Mar. 2006.

* cited by examiner

*Primary Examiner* — Clinton Brooks
(74) *Attorney, Agent, or Firm* — Yonggang Ji

(57) ABSTRACT

The invention relates to new processes for preparation of $^{18}$F-fluoroalkyl halides suitable for use in labelling of Positron Emission Tomography (PET) radiotracers. The process of preparation comprises the step of reacting a $^{18}$F-fluoroacylhalide with Wilkinson's catalyst.

8 Claims, No Drawings

METHOD FOR THE PREPARATION OF [¹⁸F]FLUOROALKYLHALIDES

This application is a filing under 35 U.S.C. 371 of international application number PCT/NO2006/000473, filed Dec. 8, 2006, which claims priority to application number 0524988.3 filed Dec. 8, 2005, in Great Britain the entire disclosure of which is hereby incorporated by reference.

The invention relates to new processes for preparation of [¹⁸F]fluoroalkyl halides suitable for use in labelling of Positron Emission Tomography (PET) radiotracers.

The favoured radioisotope for PET, ¹⁸F, has a relatively short half-life of 110 minutes. ¹⁸F-labelled tracers for PET therefore have to be synthesised and purified as rapidly as possibly, and ideally within one hour of clinical use. PET tracers are frequently labelled with [¹⁸F]fluoroalkyl groups to produce [¹⁸F]fluoroalkylated PET tracers. [¹⁸F]fluoroalkyl halides are important reagents for performing O—, N—, and S— [¹⁸F]fluoroalkylations, such as [¹⁸F]fluoromethylations, and are commonly used to radiolabel radiotracers for use in PET studies.

[¹⁸F]Fluoroalkyl halides have previously been prepared by nucleophilic displacement, by [¹⁸F]F⁻, of a leaving group from a suitable precursor compound. Thus, for example Zhang et al, Applied Radiation and Isotopes 57, 335-342 (2002), describes synthesis of [¹⁸F]fluoroethyl bromide by nucleophilic displacement of 2-trifluoromethanesulphonyloxy ethylbromide with ¹⁸F⁻ and Seung-Jun et al, Applied Radiation and Isotopes (1999), 51, 293-7 describes an analogous synthesis of 3-[¹⁸F]fluoropropylbromide. A similar method is described in Comagic et al, Applied Radiation and Isotopes (2002), 56, 847-851 wherein 2 bromo-1-[¹⁸F]fluoroethane is prepared by nucleophilic displacement of 1,2 dibromoethane with ¹⁸F⁻. Solid-phase preparations of [¹⁸F] fluoroalkyl halides are described in WO 2004/056726 which discloses a process for preparation comprising the treatment of a solid support-bound precursor of the formula solid support linker-SO₂—O—(CH₂)ₙX, wherein n is an integer of from 1 to 7 and X is chloro, bromo or iodo, with ¹⁸F⁻.

Unfortunately, production of [¹⁸F]fluoroalkylation reagents, such as the corresponding bromide and triflate, is complicated. The drawbacks with existing processes are complicated purification, relatively long preparation times and non-optimal yields.

In view of the importance of [¹⁸F]fluoroalkyl halides as radiolabelling reagents, there exists a need for new synthetic methods for their preparation in good radiochemical yield and of high purity. Furthermore, there is also a need for such synthetic methods which are less complicated and more automatic.

In a first aspect, the present invention provides a process for the preparation of [¹⁸F]fluoroalkylation reagents, particularly [¹⁸F]fluoroalkyl halides of formula (I)

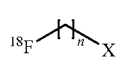

(I)

wherein n is an integer from 1 to 6 and X is a halide. More preferably n is an integer 1 or 2 and X is chloride, bromide or iodide.

In one embodiment the invention provides a process for the preparation of [¹⁸F]fluoroalkyl halides of formula (I) comprising the step of reacting a [¹⁸F]fluoroacylhalide of formula (II),

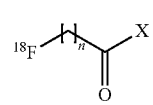

(II)

wherein X represents a halide and n represents an integer from 1 to 6, with Wilkinson's catalyst.

The reaction is disclosed in scheme 1.

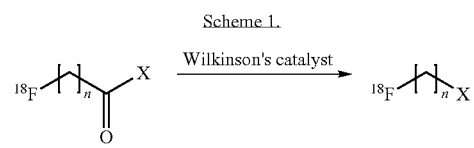

Scheme 1.

X represents a halide, preferably chloride, bromide or iodide and most preferably chloride or bromide. n is preferably 1 or 2.

Wilkinson's catalyst is a rhodium metal complex with three large phosphine ligands coordinated to the metal centre, Rh(PPh₃)₃Cl, i.e. chlorotris(triphenyl-phosphine)rhodium (I). The organometallic compound activates small organic molecules such that bond-breaking and bond-formation pathways are readily accessible. The catalyst is widely used in the hydrogenation of alkenes under mild conditions and is also known to readily react with acylhalides at ambient temperature to give the corresponding decarbonylated compounds. Acetyl chloride is e.g. transformed to methyl chloride under activation by Wilkinson's catalyst.

A drawback associated with the catalyst is however that the carbonylated catalyst is regenerated only at high temperatures. This problem has been overcome by using diphenylphosphonic azide (Ph₂P(O)N₃), as disclosed in J Org Chem 1992, 57, 5075, together with Wilkinson's catalyst. Diphenylphosphonic azide is commercially available. In a preferred embodiment the process for preparation according to Scheme 1 includes use of equimolar amounts of the acylhalide and diphenylphosphonic azide, or more preferably an excess of the diphenylphosphonic azide. In the presence of this reagent the reaction goes readily at ambient temperature with only catalytic amounts of Wilkinson's catalyst, typically 1-20%, more preferably 2-10% and most preferably about 5% in molar amounts.

The reaction step of this first embodiment is preferably carried out without any solvents, but addition of any solvents that would promote the reaction could be included. Suitable such solvents would be e.g. acetonitrile, dichloromethane (DCM), dimethylformamide (DMF), dimethyl sulfoxide (DMSO) and tetrahydrofurane (THF).

The [¹⁸F]fluoroacylhalide starting material of formula (II) is readily prepared in a process treating a haloacylhalide of formula (III)

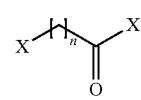

(III)

wherein X represents a halide, and wherein preferably both X-groups are the same halide, and n represents an integer from 1 to 6, with [¹⁸F]-fluoride.

When a haloacylhalide (III) is treated with [$^{18}$F]-fluoride two reactions will occur: i) formation of haloacyl fluorides and ii) formation of fluoroacylhalides (II) wherein either of the halides of the haloacylhalide is substituted with an $^{18}$F-atom. Since the first reaction is reversible and the second reaction irreversible the final product will be fluoroacylhalides (II), as long as the haloacylhalide (III) is added in excess. The reaction is disclosed in scheme 2.

Scheme 2.

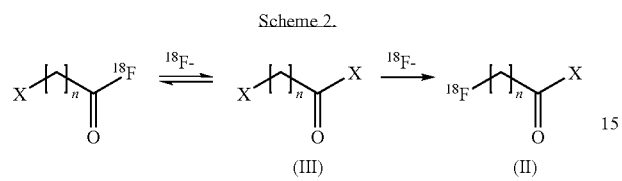

(III)  (II)

X represents a halide, preferably chloride, bromide or iodide and most preferably chloride or bromide. n is preferably 1 or 2.

The fluorination step is optionally followed by
(i) removal of excess $^{18}$F$^-$, for example by ion-exchange chromatography; and/or
(ii) removal of organic solvent.

The treatment with $^{18}$F$^-$ may be effected by treatment with any suitable source of $^{18}$F$^-$, such as Na$^{18}$F, K$^{18}$F, Cs$^{18}$F, tetraalkylammonium $^{18}$F fluoride, or tetraalkylphosphonium $^{18}$F fluoride. To increase the reactivity of the fluoride, a phase transfer catalyst such as an aminopolyether or crown ether, for example, 4,7,13,16,21,24 hexaoxa-1,10-diazabicyclo[8,8,8]hexacosane (Kryptofix 2.2.2.) may be added and the reaction performed in a non protic solvent. These conditions give reactive fluoride ions. Optionally, a free radical trap may be used to improve fluoridation yields, as described in WO 2005/061415. The term "free radical trap" is defined as any agent that interacts with free radicals and inactivates them. A suitable free radical trap for this purpose may be selected from 2,2,6,6-Tetramethylpiperidine-N-Oxide (TEMPO), 1,2-diphenylethylene (DPE), ascorbate, para-amino benzoic acid (PABA), α-tocopherol, hydroquinone, di-t-butyl phenol, β-carotene and gentisic acid. Preferred free radical traps for use in the process of the invention are TEMPO and DPE, with TEMPO being most preferred.

The treatment with $^{18}$F$^-$ is suitably effected in the presence of a suitable organic solvent such as acetonitrile, dimethylformamide, dimethyl sulfoxide, tetrahydrofuran, dioxane, 1,2 dimethoxyethane, sulfolane, N-methylpyrrolidone, at a non-extreme temperature, for example, 15° C. to 180° C., preferably at elevated temperature, such as 80° C. to 150° C., for example around 120° C. On completion of the reaction, the [$^{18}$F]fluoroacylhalide may be purified and separated from the solvent, preferably by distillation. Preferably however, the crude product, the $^{18}$F-fluoroacylhalide (II), is used directly in the next step for preparation of a $^{18}$F-fluoroalkylhalide (I).

Any excess $^{18}$F$^-$ may optionally be removed from the solution of the $^{18}$F-labelled compound by any suitable means, for example by distillation or alternatively by ion-exchange chromatography or solid phase absorbents. Suitable ion-exchange resins include BIO-RAD AG 1-X8 or Waters QMA and suitable solid phase absorbents include alumina. The excess $^{18}$F$^-$ may be removed using such solid phases at room temperature in aprotic solvents.

Conveniently this embodiment provides a process for the preparation of a [$^{18}$F]fluoroalkyl halide of formula (I)

comprising the steps of
i) treating a haloacylhalide of formula (III)

with $^{18}$F-fluoride to generate a [$^{18}$F]fluoroacylhalide of formula (II),

followed by
ii) treating the [$^{18}$F]fluoroacylhalide of step (i) with Wilkinson's catalyst, wherein X represents a halide and n represents an integer from 1 to 6.

The complete process for preparation of [$^{18}$F]fluoroalkyl halide according to this embodiment is disclosed in scheme 3, wherein a haloacylhalide (III) is the starting material. The second step preferably includes use of diphenylphosphonic azide as described. X represents a halide, preferably chloride, bromide or iodide, and is preferably chloride. n is an integer from 1 to 6 and is preferably 1 or 2.

Scheme 3.

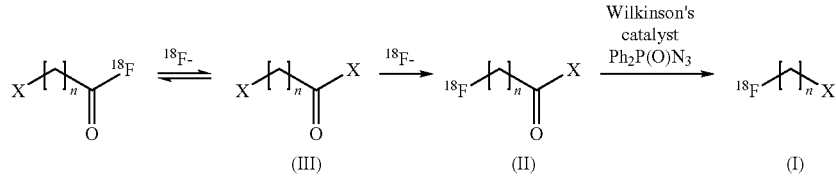

(III)  (II)  (I)

The process for preparation according to this embodiment is preferably a self-purifying formation of [$^{18}$F]fluoroalkyl halides of formula (I), meaning that the [$^{18}$F]fluoroalkyl halide prepared is obtained in a purity of at least 94%, preferably at least 96% and most preferably at least 98 mol %, without performing any separate purification step of the product.

The reaction with Wilkinson catalyst is exothermic, and in a preferred aspect the prepared [$^{18}$F]fluoroalkyl halide will spontaneously distil out of the reaction mixture and in this way being self-purified. When using the crude product, the $^{18}$F-fluoroacylhalide (II), from step (i) directly in the next step for preparation of a $^{18}$F-fluoroalkylhalide (I) some unreacted haloacylhalide starting material may be present in the reaction mixture. When Wilkinson's catalyst is added to the reaction mixture, the unreacted haloacylhalide will be decarbonylated forming the corresponding dihaloalkane, such as dichloromethane. For the example when n is 1 and X is chloride both dichloromethane and the prepared [$^{18}$F]fluoromethyl chloride will be spontaneously distilled out of the reaction vessel due to the exothermic reaction, and since these are by far the most volatile compounds in the mixture [$^{18}$F]fluoromethyl chloride is hence self-purified in the process. The prepared $^{18}$F-fluoroalkylhalide (I) will hence be obtained in an inert solvent, dichloromethane, originating from the starting material. The obtained $^{18}$F-fluoroalkylhalide (I) product, in the solvent, may be used directly as a reagent for performing e.g. O—, N—, and S—[$^{18}$F]fluoroalkylations of an appropriate precursor compound for preparation of an $^{18}$F-labelled compound for use in PET chemistry. In the case wherein X is iodide or bromide the [$^{18}$F]fluoroalkyl halide should still be very volatile but a low boiling solvent such as dichloromethane or an ether would need to be added to help distil out the product. In a small scale production wherein small quantities of the acyl halide is used the energy released in the process might be insufficient for self-distillation and external heating will be required.

One benefit of the process of preparation according to scheme 3, from conventional methods, is that some of the haloacylhalide starting reagent is converted into a suitable solvent and that the other reagents are non-volatile, making separation from any reagents and bi-products easy. The process of preparation hence provides a method of preparing [$^{18}$F]fluoroalkyl halides of high purity in an uncomplicated process.

If chloro acyl chloride (X is chloride) is used as starting material in the above reaction (scheme 3) the product will be a [$^{18}$F]fluoroalkyl chloride, such as [$^{18}$F]fluoromethyl chloride. The product will distil out together with dichloromethane, which remains inert under most conditions and will serve as a co-solvent. The product can then be further transformed to e.g. the corresponding bromide or triflate which are more reactive reagents for use in [$^{18}$F]fluoroalkylations.

However, it could be advantageous with direct formation of a more reactive reagent than [$^{18}$F]fluoroalkyl chloride. One way of achieving this is to use chloroacyl chloride as the starting material and add a nucleophile which is better than chloride to the reaction mixture, in either of the steps, making sure it is present under the decarbonylation reaction, such as adding a bromide nucleophile, e.g. lithium bromide (LiBr). Since bromide is a much better nucleophile than chloride, the fluoralkyl group should be cleaved from the catalyst by bromide instead of chloride, preparing [$^{18}$F]fluoroalkyl bromide. Another possibility is to start with a bromo acyl bromide (X is bromide), a drawback of this approach is however the reactivity of this reagent towards moisture.

If X in formula (III) is iodide a [$^{18}$F]fluoroalkyl iodide will be formed. As an alternative [$^{18}$F]fluoroalkyl iodide may be prepared using chloroacyl chloride as the starting material, and add a iodide nucleophile, such as e.g. lithium iodide (LiI) to the reaction mixture. Since iodide is a better nucleophile than chloride, the fluoroalkyl group should be cleaved from the catalyst by iodide instead of chloride, preparing [$^{18}$F]fluoroalkyl iodide.

The radiochemical yield of the process of the first embodiment is more than 50%, preferably more than 60% and most preferably more than 70%.

As a second embodiment, the invention provides a process for preparation of [$^{18}$F]fluoroalkyl halides of formula (I) using a solid phase approach. The process comprises generation of a [$^{18}$F]fluoroacylhalide of formula (II) by an alternative route to the route of the first embodiment, for further reaction with Wilkinson's catalyst to prepare a [$^{18}$F]fluoroalkyl halide.

In this embodiment, a process for the preparation of [$^{18}$F] fluoroacylhalide of formula (II) comprises a first step of reacting [$^{18}$F]fluoride with a solid phase resin functionalised with an alkylic acid group of Formula (IV),

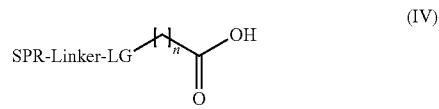

(IV)

wherein

SPR represents a solid phase resin,

LG represents a leaving group; and

N represents an integer from 1 to 6.

The alkylic acid group is attached to the solid resin by means of a leaving group between the resin and the allylic acid group. The leaving group is suitably selected from the group of mesylate (OMe), tosylate (OTs), triflate (OTf) and nosylate (ONs), and is preferably tosylate. n is an integer from 1 to 6 and is preferably 1 or 2.

The linker may be any suitable organic group which serves to space the resin from the reactive site so as to maximise reactivity. Alternatively, the linker is simply a covalent bond. Suitably, the linker comprises zero to four aryl groups (suitably phenyl) and/or a $C_1$-$C_6$-alkyl or $C_1$-$C_6$-haloalkyl, typically $C_1$-$C_6$-fluoroalkyl, or $C_1$-$C_6$-alkoxy or $C_1$-$C_6$-haloalkoxy typically $C_1$-$C_6$-fluoroalkoxy, and optionally one to four additional functional groups such as amide or sulfonamide groups. Examples of such linkers are well known to those skilled in the art of solid-phase chemistry.

When reacting the compound of Formula (IV) with [$^{18}$F] fluoride a [$^{18}$F]fluoroalkylic acid is formed.

As a second reaction step in the preparation of a [$^{18}$F] fluoroacylhalide a halide-containing nucleophile and triphenylphosphine (PPh$_3$) is added to the [$^{18}$F]fluoroalkylic acid generated in the first step. Suitable halide-containing nucleophiles are e.g. carbon tetrabromide (CBr$_4$), bromine (Br$_2$), carbon tetrachloride (CCl$_4$), chloride (Cl$_2$), carbon tetraiodide (CI$_4$) or iodide (I$_2$).

The reaction is disclosed in scheme 4 wherein

SPR represents a solid phase resin,

LG represents a leaving group, n represents an integer from 1 to 6; and

X' represents a halide-containing nucleophile.

The halide-containing nucleophile, X', comprises the same halide, X, as the generated [$^{18}$F]fluoroacylhalide.

Scheme 4

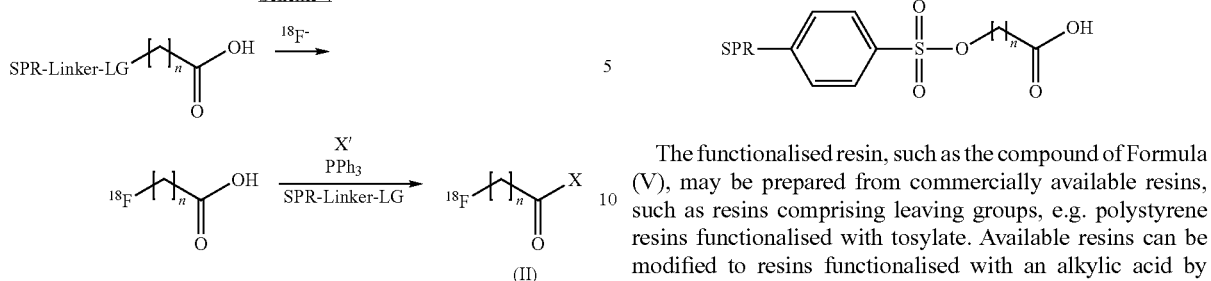

Conveniently, this embodiment provides a process for the preparation of a [$^{18}$F]fluoroalkyl halide of formula (I),

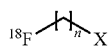 (I)

comprising the steps of preparing a [$^{18}$F]fluoroacylhalide of formula (II)

(II)

wherein X represents a halide and n represents an integer from 1 to 6, by a) reacting [$^{18}$F]fluoride with a solid phase resin functionalised with an alkylic acid group, preparing a [$^{18}$F]fluoroalkylic acid, followed by b) reacting the [$^{18}$F]fluoroalkylic acid of step (a), with a halide-containing nucleophile.

The solid phase resin may be any suitable solid phase resin which is or can be functionalised with an alkylic acid group. The resin should preferably experience a reasonable swelling in the solvent of choice. Examples of suitable resins include polymers such as polystyrene, polyamide, polyacrylamide, polypropylene, a ring opening metathesis polymer (ROMP gel), or glass or silicon coated with a polymer. In a preferred aspect the solid phase resin is based on polystyrene or ROMP gel.

The triphenyl phosphine is preferably added in the form of a resin. Hence, there is preferably one resin for the starting material and another for the PPh$_3$ reagent. The PPh$_3$ reagent is preferably added in the form of triphenylphoshine attached to a polystyrene or ROMP gel resin. Such resins are commercially available.

The solid phase resins may be in the form of small discrete particles such as beads or pins, or as a coating on the inner surface of a cartridge or on a microfabricated vessel.

The functionalised resin preferably comprises an alkylic acid group linked to a solid phase resin via a toluenesulfonyl group (tosylate). One such group is disclosed in Formula (V), wherein SPR represents a solid phase resin and n represents an integer from 1 to 6.

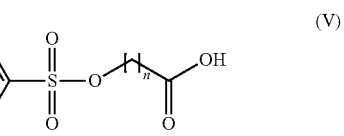 (V)

The functionalised resin, such as the compound of Formula (V), may be prepared from commercially available resins, such as resins comprising leaving groups, e.g. polystyrene resins functionalised with tosylate. Available resins can be modified to resins functionalised with an alkylic acid by reaction with e.g. Y—(CH$_2$)$_n$COOH wherein Y is selected from e.g. hydroxyl or the deprotonated oxycarboxylate (i.e. treatment with 2 equivalents of base). This reagent can then be reacted with corresponding chlorides (halides) of the leaving group of the resin, e.g. with a tosyl chloride as shown below. A third option is to make the leaving group attached to the alkylic acid first and attach this to a polymer afterwards. Methods for preparing such functionalised solid phase resins are well known to those skilled in the art of solid phase chemistry. One alternative example of preparation of compounds according to Formula (V) is shown in scheme 5.

Scheme 5

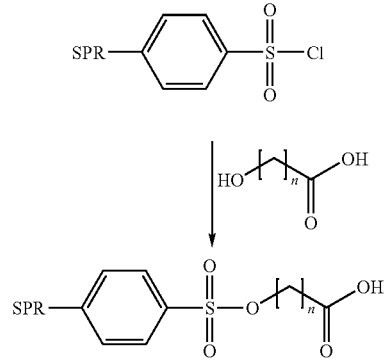

According to the process of this embodiment, using an alkylic acid group attached to a solid phase resin by means of a leaving group as the starting material, addition of $^{18}$F-fluoride will liberate the $^{18}$F-containing acyl groups, while the remaining starting material will stay on the resin. When a [$^{18}$F]fluoroalkylic acid has been formed, addition of a halide-containing nucleophile, such as e.g. CBr$_4$, will lead to formation of the corresponding [$^{18}$F]fluoroacylhalide of formula (II). The reaction is preferably performed in presence of triphenylphosphine, either added separately or as attached to a solid phase resin.

Conveniently, this embodiment further comprises the step of decarbonylating the [$^{18}$F]fluoroacylhalide of formula (II) generated in the solid phase approach with Wilkinson's catalyst according to the first embodiment of the invention. Wilkinson's catalyst is optionally attached to a solid phase resin. In this embodiment however, no addition of diphenylphosphonic azide is needed. The complete process for preparation of a [$^{18}$F]fluoroalkyl halide of formula (I) according to this embodiment is disclosed in scheme 6 wherein
SPR represents a solid phase resin,
LG represents a leaving group,
N represents an integer from 1 to 6; and
X' represents a halide-containing nucleophile.

Scheme 6

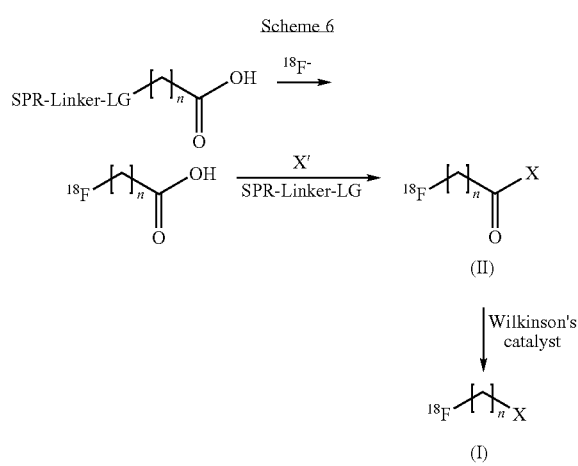

One advantage of solid supported reagents is that reagents that normally will react with each other can be kept together in a reaction vessel when they all are supported, since there are no means for the reagents to actually meet. With respect to the reagents relevant to this invention, triphenylphosphine is available supported on both polystyrene and ROMP gel, and Wilkinson's catalyst is available supported on ROMP gel.

Conveniently, in this embodiment the reaction sequence preparing [$^{18}$F]fluoroalkyl halide according to scheme 6 is prepared in a one-pot formation, wherein all reagents, including the solid phase resins and the catalyst, are kept together in one reaction vessel. The [$^{18}$F]fluoroalkyl halide end product can then be obtained by simple filtration. A silica plug may optionally be used to remove any phase transfer catalysts, optionally used during the fluorination. It may or may not be required to substitute the chloride counter ion in Wilkinson's catalyst with a non nucleophilic anion, e.g. methylsulfonate, to avoid competing reactions between fluoride and chloride in the reaction sequence.

As described above, the advantages of such solid-phase processes for preparation of [$^{18}$F]fluoroalkyl halides include the relative speed of the process, simplified purification methods and ease of automation, all of which mean that the processes are suitable for preparation of [$^{18}$F]fluoroalkyl halides which can then be used to prepare $^{18}$F-labelled tracers for use in PET.

The [$^{18}$F]fluoroalkyl halides prepared by the processes of the present invention may be used in preparation of further [$^{18}$F]fluoroalkyl reagents wherein the halide is substituted with other leaving groups. The halide may be substituted according to standard literature methods, such as e.g. changing from halide to triflate by heating the [$^{18}$F]fluoroalkyl halide on AgOTf.

Conveniently, the solid phase resin bound precursor of formula (IV) could be provided as part of a kit to a radiopharmacy, PET centre, or nuclear medicine department. The kit may contain a cartridge which can be plugged into a suitably adapted automated synthesiser. The cartridge may contain, apart from a vessel for preparation of a [$^{18}$F]fluoroalkyl halide according to the invention, a column to remove unwanted fluoride ion, and an appropriate vessel comprising a precursor compound to be fluoroalkylated with the generated [$^{18}$F]fluoroalkyl halide, connected so at to allow the product to be formulated as required. The reagents, solvents, and solid phase resins and other consumables required for the synthesis may also be included together with a compact disc carrying the software which allows the synthesiser to be operated in a way so as to meet the customer's requirements for radioactive concentration, volumes, time of delivery etc.

Conveniently, all components of the kit are disposable to minimise the possibilities of contamination between runs and may be sterile and quality assured.

As a further aspect the invention hence provides a radiopharmaceutical kit for the preparation of an $^{18}$F-labelled compound for use in PET chemistry, which comprises
i) a first vessel for preparation of a [$^{18}$F]fluoroalkyl halide of formula (I) according to either of the processes of the invention;
ii) a second vessel containing a precursor compound for [$^{18}$F]fluoroalkylation with the [$^{18}$F]fluoroalkyl halide; and optionally
iii) a tubing to lead the generated [$^{18}$F]fluoroalkyl halide from the first vessel into the second vessel;
iv) an ion-exchange cartridge for removal of excess $^{8}$F;

The first vessel preferably comprises means for eluting with a source of $^{18}$F$^{-}$.

The invention is illustrated by way of the following non-limiting examples.

EXAMPLES

Example 1

Synthesis of [$^{18}$F]Fluoroacetyl Chloride

A reaction vessel is charged with chloroacetyl chloride (1 equivalent) with or without a solvent, for example acetonitrile or dimethylsulfoxide, and a mixture of potassium $^{18}$F-fluoride, Kryptofix and potassium carbonate. The reaction mixture is heated to a temperature between 80-150° C. in a sealed system. The crude material is cooled and used directly in the subsequent step.

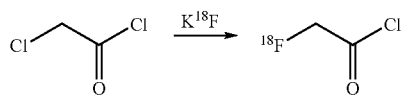

Example 2

Synthesis of [$^{18}$F]Fluoroacetyl Bromide

A reaction vessel is charged with bromoacetyl bromide (1 equivalent) with or without a solvent, for example acetonitrile or dimethylsulfoxide, and a mixture of potassium $^{18}$F-fluoride, Kryptofix and potassium carbonate. The reaction mixture is heated to a temperature between 80-150° C. in a sealed system. The crude material is cooled and used directly in the subsequent step.

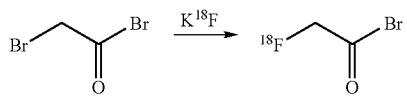

Example 3

Synthesis of [$^{18}$F]fluoromethyl Halides

The fluoroacetyl halides generated in example 1 and 2 are transformed into [$^{18}$F]fluoromethyl chloride and [$^{18}$F]fluoromethyl bromide, respectively, under activation of catalytic amounts (2-20%) of Wilkinson's catalyst $(Rh(PPh_3)_3Cl)$ in the presence of molar excess of diphenylphosphonic azide. This results in an exothermic reaction that converts the alpha-fluoroacetyl halide to the corresponding fluoromethyl halides, and any unreacted alpha-haloacetyl halide will be converted to the corresponding dihalomethane. Spontaneous or forced distillation will provide the pure [$^{18}$F]fluoromethyl halide in the solvent mixture from the initial reaction.

Example 4

Synthesis of [$^{18}$F]Fluoromethyl Iodide by Solid Phase Approach

To polystyrene supported potassium alpha-tosyl acetate, polystyrene supported triphenylphosphine and polystyrene supported Wilkinson's catalyst is added a solution of potassium $^{18}$F-fluoride and Kryptofix in a suitable solvent (dichloromethane, tetrahydrofurane or acetonitrile) and the mixture is heated in a sealed vial to 40-120° C. for 5-30 minutes. When the formation of potassium alpha-[$^{18}$F]fluoroacetate has gone to completion tetraiodomethane is added and the reaction is heated to 40-120° C. for 5-30 minutes to produce alpha-[$^{18}$F]fluoroacetyl iodide, which in contact with Wilkinson's catalyst will be converted to $^{18}$F-fluoromethyliodide. Filtration of the mixture, with or without filtration through a silica plug, provides the $^{18}$F-fluoromethyliodide in the given reaction solvent void of any reagents that interfere with any further nucleophilic alkylation.

What is claimed is:

1. A process for the preparation of a [$^{18}$F]fluoroalkyl halide of formula (I)

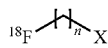
(I)

comprising the steps of
i) treating a haloacylhalide of formula (III)

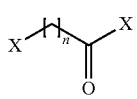
(III)

with $^{18}$F-fluoride to generate a [$^{18}$F]fluoroacylhalide of formula (II),

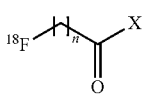
(II)

followed by
ii) treating the [$^{18}$F]fluoroacylhalide of step (i) with Wilkinson's catalyst, wherein X represents a halide and n represents an integer from 1 to 6; and wherein the prepared [$^{18}$F]fluoroalkyl halide is purified by being spontaneously distilled out from the reaction mixture.

2. A process as claimed in claim 1 wherein step (ii) comprises the addition of diphenylphosphonic azide to the reaction.

3. A process as claimed in claim 1 wherein n is 1 or 2.

4. A process as claimed in claim 1 wherein the crude product from step (i) comprising the [$^{18}$F]fluoroacylhalide is used directly in step (ii) without any purification.

5. A process for the preparation of a [$^{18}$F]fluoroalkyl halide of formula (I)

(I)

comprising the step of preparing a [$^{18}$F]fluoroacylhalide of formula (II)

(II)

wherein X represents a halide and n represents an integer from 1 to 6,
by
a) reacting [$^{18}$F]fluoride with a solid phase resin functionalised with an alkylic acid group, preparing a [$^{18}$F]fluoroalkylic acid, followed by
b) reacting the [$^{18}$F]fluoroalkylic acid of step (a), with a halide-containing nucleophile; wherein step (b) further comprises the addition of triphenyl phosphine to the reaction.

6. A process as claimed in claim 5 wherein the functionalised solid phase resin is of formula (IV),

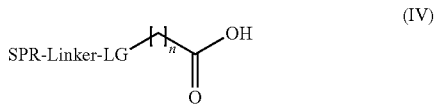
(IV)

wherein
SPR represents a solid phase resin,
LG represents a leaving group; and
N represents an integer from 1 to 6.

7. A process as claimed in claim 5 wherein step (b) is followed by treating the prepared [$^{18}$F]fluoroacylhalide with Wilkinson's catalyst to prepare the [$^{18}$F]fluoroalkyl halide of formula (I).

8. A process as claimed in claim 7 comprising a one-pot formation of a [$^{18}$F]fluoroalkyl halide of formula (I) wherein all reagents are kept together in one reaction vessel.

* * * * *